United States Patent [19]
Scribner

[11] 4,211,876
[45] Jul. 8, 1980

[54] 3-PYRAZOLIDINONE CARBOXAMIDES

[75] Inventor: Richard M. Scribner, Wilmington, Del.

[73] Assignee: E. I. Du Pont de Nemours and Company, Wilmington, Del.

[21] Appl. No.: 48,228

[22] Filed: Jun. 13, 1979

[51] Int. Cl.$^2$ ............................................. C07D 231/08
[52] U.S. Cl. .................................. 548/367; 424/273 P
[58] Field of Search .......................................... 548/367

[56] References Cited
U.S. PATENT DOCUMENTS 3,873,566  3/1975  Scribner ................................. 548/367
4,032,533  6/1977  Scribner ................................. 260/302 D

FOREIGN PATENT DOCUMENTS 2323193  11/1973  Fed. Rep. of Germany .

OTHER PUBLICATIONS

Maddox et al., Nature, 1978, v. 273, pp. 549–552.

Primary Examiner—Alan L. Rotman
Assistant Examiner—Natalia Harkaway

[57] ABSTRACT

3-Pyrazolidinone carboxamides such as N(tertamyl)7[3-oxo-1(3-hydroxy-n-octyl)pyrazolidin-2-yl]-heptanamide exhibit prostaglandin antagonist activity.

10 Claims, No Drawings

3-PYRAZOLIDINONE CARBOXAMIDES

BACKGROUND OF THE INVENTION

This invention relates to pyrazolidinones and, more particularly, to 3-pyrazolidinone carboxyamides which are prostaglandin antagonists.

U.S. Pat. No. 3,873,566 discloses and claims compounds of the general formula

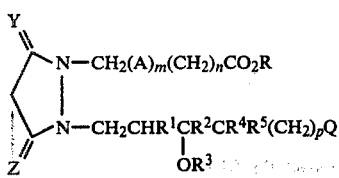

where
A can be CH=CH, C≡C or $C_6H_4$;
R can be H, alkali metal, amine salt and alkyl and cycloalkyl each with up to 12 carbons;
m is 0 or 1;
n and p are 0 to 6;
Y and Z are 0 or $H_2$, with the proviso that where one is O, the other is $H_2$;
$R^1$ is H, $CH_3$ or $C_2H_5$;
$R^2$ is H, $CH_3$, $C_2H_5$, CH=$CH_2$ or C≡CH;
$R^3$ is H or alkanoyl of 2 to 4 carbons;
$R^4$ and $R^5$ are H, F, $CH_3$ or $C_2H_5$ and
Q is H, $CH_3$, $CF_2CH_3$ or $CF_3$.
It is stated that some of the esters and acids disclosed therein inhibit or prevent experimentally-induced ulcers in rats. It is also taught that some of the esters are prostaglandin antagonists in in vitro tests employing strips of rat uterus.

U.S. Pat. No. 4,032,533 discloses 3,4-disubstituted-1,3,4-thiadiazoline-2,5-diones of the formula

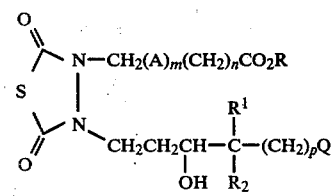

and states that the compounds are prostaglandin mimics or prostaglandin inhibitors.

German Pat. No. 2,735,904 relates to compounds of the formula

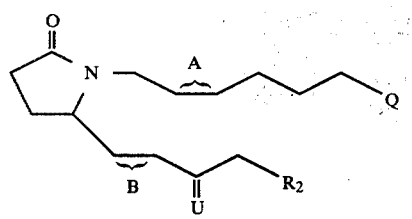

where, among other things, A and B are single or double bonds, U is

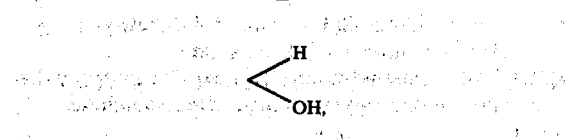

$R^2$ is phenyl or phenoxy, and Q is

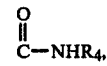

$R_4$ being selected from $COR_5$ and $SO_2R_5$ where $R_5$ is phenyl or alkyl of 1–5 carbons. These compounds are imides and are described as having prostaglandin activities which are more selective, powerful and longer lasting than the natural compounds and as having anti-ulcer and vasodilating effects.

None of these patents indicates that the compounds of this invention would exhibit prostaglandin antagonist activity.

SUMMARY OF THE INVENTION

It has been discovered that 3-pyrazolidinone carboxamides of Formula I,

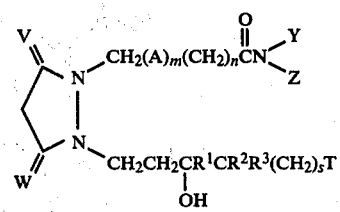

and salts with pharmaceutically acceptable acids.

where
V or W is =O and the other is $H_2$;
A is CH=CH, C≡C, or phenylene;
m is 0–1;
n is 1–5, with the proviso that when m=0, n is 5 and when m=1 and A is CH=CH or C≡C, n is 3, and when A is phenylene, n is 1, 2 or 3;
Y and Z are either the same or different and are selected from H, $C_1$–$C_{12}$ straight-chained or branched-chain alkyl;
$R^1$ is H, $CH_3$, $C_2H_5$, CH=$CH_2$, or C≡CH;
$R^2$ is H, F, or $CH_3$;
$R^3$ is H, F, or $CH_3$, with the proviso that when $R^1 \neq$ H, $R^2$ and $R^3$ are H;
s is 3–6; and
T is H, $CF_2CH_3$, or $CF_3$;
unexpectedly exhibit prostaglandin antagonist activity.

Preferred for ease of synthesis, cost and/or pharmaceutical activity are the following compounds:
N(tert-amyl)7[3-oxo-1(3-hydroxy-n-octyl)pyrazolidin-2-yl]heptanamide;
N(tert-butyl)7[3-oxo-2-(3-hydroxy-n-octyl)pyrazolidin-1-yl]heptanamide;
N(2,2-dimethylpropyl)7-[3-oxo-2(3-hydroxy-n-octyl)-pyrazolidin-1-yl]heptanamide;
N,N(diisopropyl)7-[3-oxo-2(3-hydroxy-n-octyl)-pyrazolidin-1-yl]heptanamide; and
N(1,1,3,3-tetramethyl-n-butyl)7[3-oxo-2(3-hydroxy-n-octyl)pyrazolidin-1-yl]heptanamide
N(tert-butyl)7[3-oxo-2-(3-methyl-n-octyl)pyrazolidin-1-yl]-heptanamide
N(1,1,3,3-tetramethyl-n-butyl)7-[3-oxo-2(3-hydroxy-3-methyl-n-octyl)pyrazolidin-1-yl]heptanamide N(tert-butyl)7[3-oxo-2(3-hydroxy-4,4-dimethyl-n-octyl)-pyrazolidin-1-yl]heptanamide
N(1,1,3,3-tetramethyl-n-butyl)7[3-oxo-2(3-hydroxy-4,4-dimethyl-n-octyl)pyrazolidin-1-yl]heptanamide.

DETAILED DESCRIPTION OF THE INVENTION

The compounds of this invention may be prepared as taught generally in U.S. Pat. No. 3,873,566, the teachings of which are incorporated herein by reference, according to the following reaction scheme.

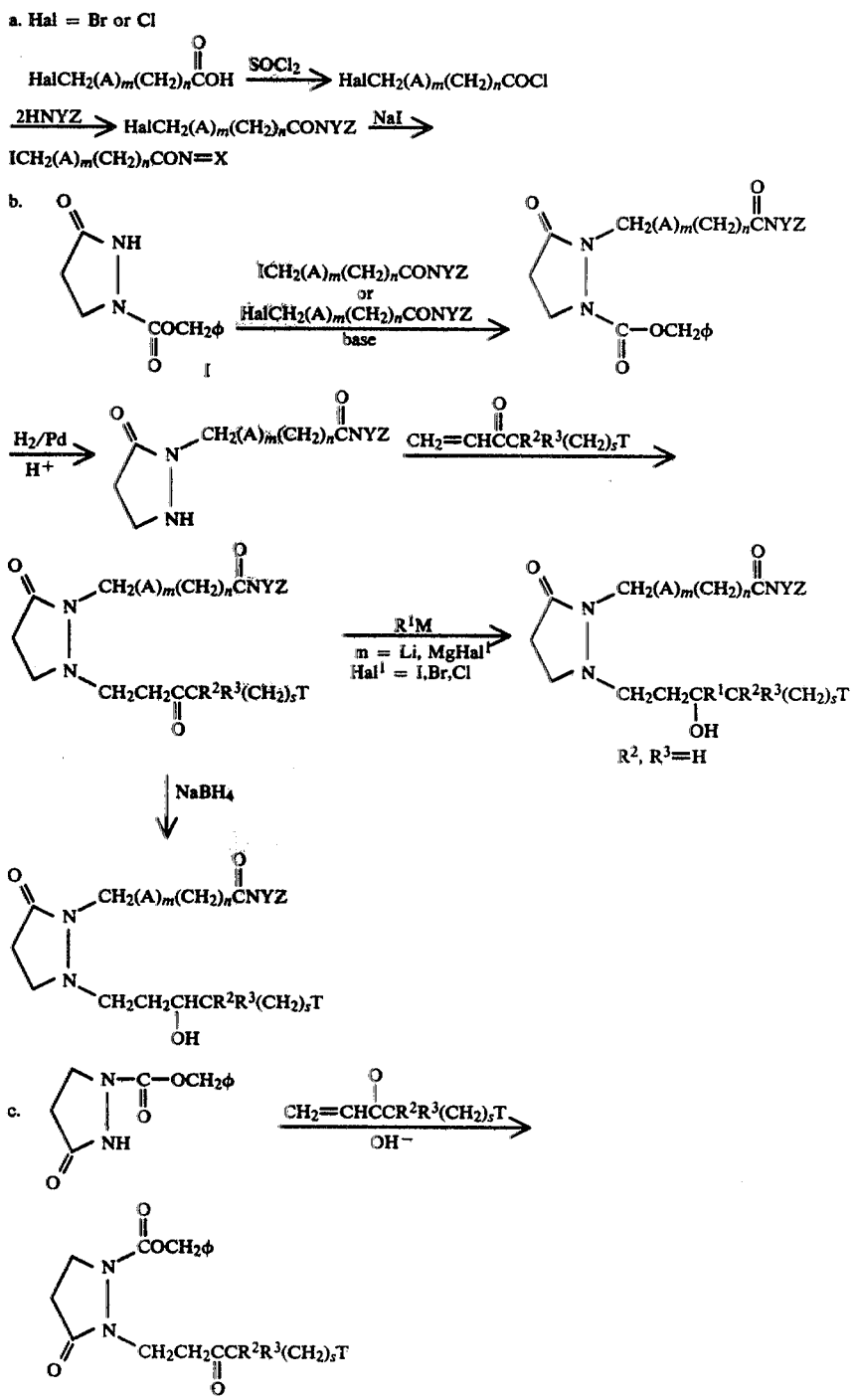

-continued

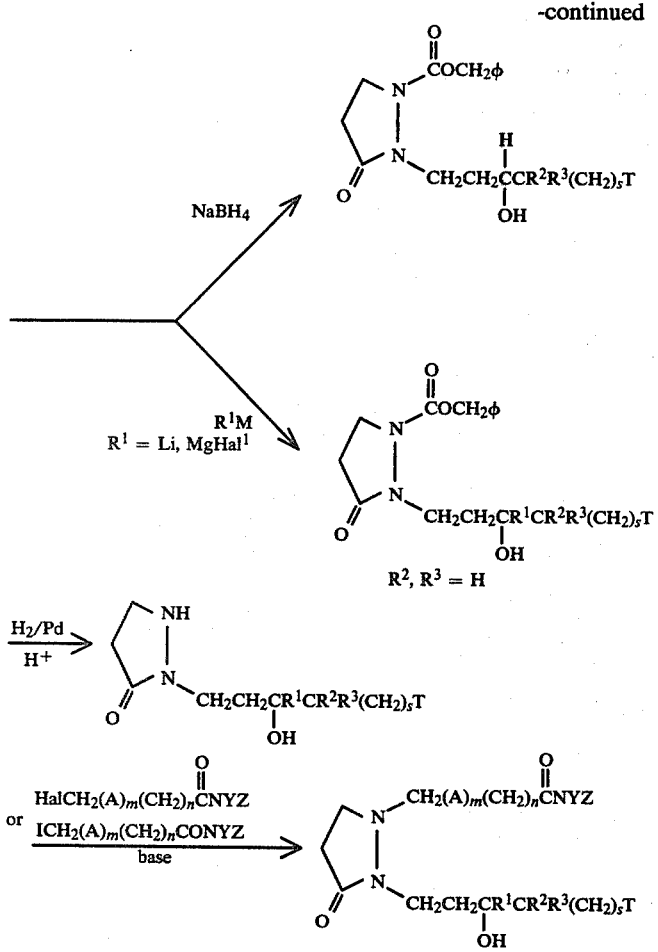

The following illustrative examples demonstrate ways of carrying out this invention. All parts and percentages are by weight, and all temperatures are in degrees Centigrade unless otherwise stated. The compounds are generally prepared as racemic forms.

EXAMPLE 1

N-(tert-butyl)-7[3-oxo-1(3-hydroxy-n-octyl)pyrazolidin-2-yl]heptanamide. (V=O, W=H$_2$, m=O, n=5, Y=H, z=tBu, R$^1$, R$^2$, R$^3$=H, s=4, T=H)

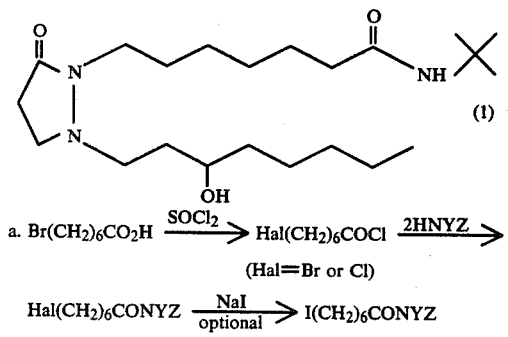

Addition of 7-bromoheptanoic acid (0.5 mole) to neat thionyl chloride (1.0 mole) plus dimethylformamide (1 ml) at 65° gave a mixture of 7-haloheptanoylchlorides that was distilled through a 12″ Vigreux column. The mixture boiled at 88°–97°/1.5 mm and contained the 7-bromo- and 7-chloroheptanoyl chlorides in the ratio of about 83:17. Alternatively the acid chlorides could be prepared by the action of SOCl$_2$ on 7-bromoheptanoic acid in a solvent, e.g. toluene and hexane, and the mixture of acid chlorides used directly or isolated by distillation.

Dropwise addition of an ether solution of a primary or secondary amine (2.2 moles) over 0.5–2 hours to a solution of the acid chlorides (1.0 mole) in ether at 0°–10° followed by washing of the cold mixture with H$_2$O, 5% HCl, 5% Na$_2$CO$_3$, and satd. NaCl solution (in that order) gave on evaporation of the solvent a mixture of 7-bromo and 7-chloroheptanamides in 65–75% yield. These were usually obtained as viscous oils. They were used directly or converted to the corresponding 7-iodo amides.

Finkelstein halogen exchange with NaI in refluxing methyl ethyl ketone or (less effectively) in refluxing acetone gave the 7-iodo amides from a mixture of the corresponding 7-bromo and 7-chloro amides. These were either thick oils or low melting solids.

Thus, a solution of 7-bromo- and 7-chloroheptanoyl chloride (0.15 mole) in 150 ml of ether was cooled in an ice bath while a solution of 22.5 g (0.31 mole) of t-butylamine in 20 ml of ether was added dropwise over 30 min. Isolation of the product by washing with H$_2$O, 5% HCl, 5% Na$_2$CO$_3$, etc., as described above gave 27.5 g of solid 7-haloheptanoic acid tert-butylamide, mp 43°–44° (69%); $v_{max}$ (neat) 1665, 1640 cm$^{-1}$. A solution of 21.8 g (82.5 mmoles) of N(tert-butyl)-7-haloheptanamide in warm, dry acetone was added to a solution of 13.6 g (90.8 mmoles) of NaI in 70 ml of dry acetone stirred at about 55° for 15 min. then cooled to room temperature. After 2 hours the acetone solution was filtered and evaporated. The residue was taken up in ether, washed with H₂O, dried over CaSO₄, evaporated, giving 23.1 g of N(tert-butyl)7-iodoheptanamide, mp 49°–50°.

b. N(tert-Butyl)7[3-oxo-1-benzyloxycarbonyl-pyrazolidin-2-yl]heptanamide (2)

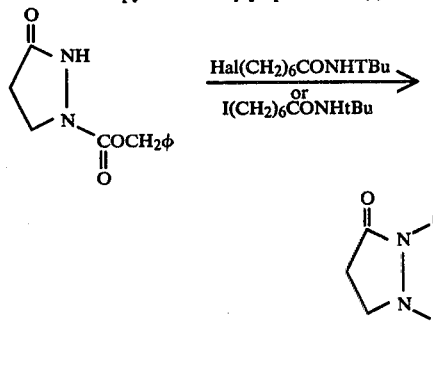

A mixture of 2.20 g (10 mmoles) of 1-benzyloxycarbonyl-3-pyrazolidinone and 3.11 g (10 mmoles) of N(tert-butyl)7-iodoheptanamide in 10 ml of dimethylformamide with 2.5 g (23.5 mmoles) of Na₂CO₃ was stirred at room temperature for 6 days. The reaction mixture was poured into water and extracted with ethyl acetate two times. Evaporation of the solvent after it had been washed with water and satd. NaCl and dried (MgSO₄) gave 4.3 g of crude N(tert-butyl)7[3-oxo-2-benzyloxycarbonyl-1(3-hydroxy-n-octyl)pyrazolidin-2-yl]heptanamide (2). Similarly reaction of 1-benzyloxycarbonyl pyrazolidinone with the corresponding 7-bromoheptanamide in dimethylformamide in the presence of Na₂CO₃ at 100° For about 5 hours gave, according to TLC, the same product. Combination of these two runs and chromatography on silica gel (HPLC, ethyl acetate) gave 4.6 g of pure 2.

High resolution mass spectroscopy of 2:

| Measured | Calcd. | assignment |
| --- | --- | --- |
| 403.2453 | 403.2469 | C₂₂H₃₃N₃O₄ (2) |
| 331.1639 | 331.1657 | M—C₄H₁₀ |
| 268.2000 | 268.2023 | M=φCH₂OCO |
| 212.1394 | 212.1398 | M—(φCH₂OCO + C₄H₈) |
| 195.1112 | 195.1133 | M—(φCH₂OCO + C₄H₁₀ + H) |

The proton magnetic resonance spectrum of the purified sample agreed with structure 2.

c. N(tert-Butyl)7[3-oxo-2-pyrazolidin-2-yl]heptanamide (3)

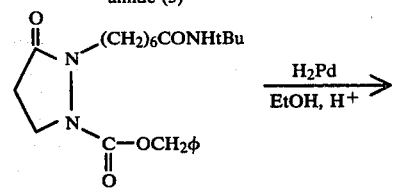

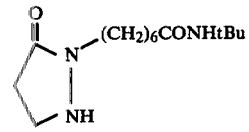

A solution of 14.5 g of 2, prepared and purified as in part b, in 200 ml of ethanol with 5.5 ml glacial acetic acid was hydrogenated at 40 psi over 1.5 g of 10% Pd/C in a Parr shaker for 1 hr. The mixture was filtered through a pad of Celite and the solvent removed under reduced pressure. To the remaining liquid, 40 ml of 1N HCl was added and the mixture was extracted with ethyl acetate thrice. The aqueous layer was then saturated with excess K₂CO₃ and extracted with ethyl acetate thrice again. The latter set of ethyl acetate extracts were dried over anhyd. K₂CO₃ and evaporated, yielding 8.45 g of colorless oil (87.5%), pure 3.

d. N(tert-Butyl)7[3-oxo-1(3-oxo-n-octyl)pyrazolidin-2-yl]heptanamide (4)

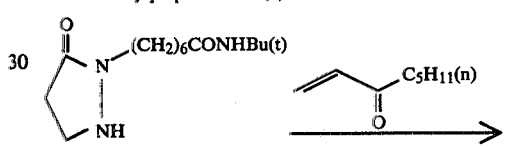

To a solution of 8.45 (31.4 mmoles) in 35 ml of ethanol was added 4.35 (34.5 mmoles) of amyl vinyl ketone in 10 ml of ethanol. The mixture was stirred at room temp. over night, affording an ethanolic solution of 4. This solution could be used directly for the (next) reduction step or the solvent could be evaporated, replaced by tetrahydrofuran or ether, and the new solution used for reaction with an organometallic alkylating reagent to obtain the C-15-alkyl C-15-ol/prostanoid.

e. N(tert-Butyl)7[3-oxo-1-(3-hydroxy-n-octyl)-pyrazolidin-2-yl]heptanamide (1)

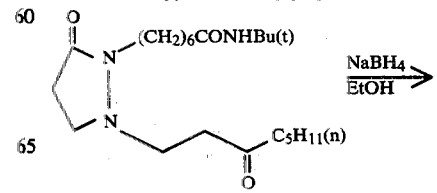

-continued

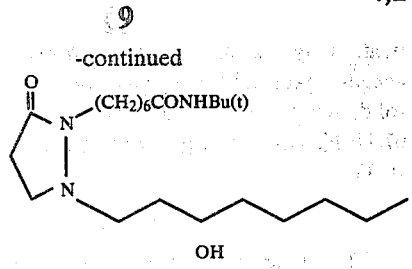

The ethanolic solution of 4 obtained as above was cooled in an ice bath and 2.5 g of NaBH$_4$ was added all at once. The mixture was stirred with cooling for 2 hrs, and then with no cooling for about 5 hrs, it was poured into water, extracted with ether twice. The ether was washed with satd. NaCl solution and dried over anhyd. K$_2$CO$_3$. TLC indicated the oil obtained (11.6 g) was about 90% pure. The oil was purified by preparative scale HPLC using 6.6% MeOH/EtOAc as the eluent. This gave 11.2 g (93% yield) of 1 as a colorless oil, $\lambda_{max}$ 3320 (OH), 1680–1650 (CO) cm$^{-1}$. HRMS spectrum

| measured | calcd. | assignment |
|---|---|---|
| 397.3330 | 397.3302 | C$_{22}$H$_{43}$O$_3$N$_2$ mol. ion |
| 326.2459 | 326.2447 | M—C$_5$H$_{11}$ |
| 325.2475 | 325.2489 | M—C$_4$H$_9$N |
| 282.2204 | 282.2180 | M—CH$_2$CH(OH)C$_5$H$_{11}$ |

The pmr spectrum agreed with the assigned structure.

EXAMPLE 2

N(tert-Amyl)7[3-oxo-1(3-hydroxy-n-octyl)pyrazolidin-2-yl]heptanamide (5) (V=O, W=H$_2$, m=O, n=5, Y=H, Z=tert-amyl)

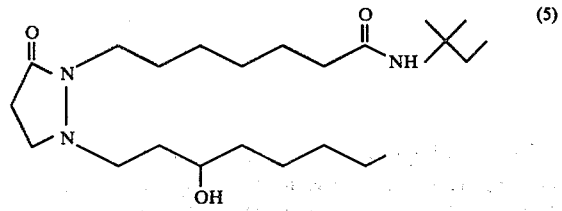

a. In a manner analogous to Example 1a, N(tert-amyl)7-bromo(chloro)heptanamide was prepared from 7-bromoheptanoic acid, SOCl$_2$, and tert- amylamine. This was converted to N(tert-amyl)7-iodoheptanamide by the action of NaI in refluxing methyl vinyl ketone for 17 hrs; the iodoamide was close to 100% pure (gas chromatography); $\lambda_{max}$ 1645 cm$^{-1}$.

b. The iodoamide (6.6 g) was stirred with 1-benzyloxycarbonyl-3-pyrazolidinone (4.4 g) and K$_2$CO$_3$ (3.5 g) in N,N-dimethylformamide for 7 days at room temp and then the mixture was heated for 2 hrs at 100°. The crude reaction product (7.7 g oil) isolated as in Example 1b, was purified by preparative scale HPLC (5% MeOH/CH$_2$Cl$_2$), giving 4.65 g of pure N(tert-amyl)-7-[3-oxo-1-benzyloxycarbonylpyrazolidin-2-yl]heptanamide. The pmr spectrum was in agreement with the assigned structure.

c. Hydrogenation of the last-named compound (4.6 g) in ethanol (200 ml) and acetic acid (2 ml) over 5% Pd/C (0.5 g) according to the procedure described in Example 1c, gave 2.54 g of N(tert-amyl)7[3-oxo-2-pyrazolidin-2-yl]heptanamide as a colorless oil; $\lambda_{max}$ 1670 cm$^{-1}$ (broad); pmr agreed well.

d. Reaction of the last-named compound (2.5 g) in ethanol (30 ml) with 1.2 g of amyl vinyl ketone at room temp for 5 hrs gave an ethanolic solution of N(tert-amyl)7[3-oxo-1(3-oxo-n-octyl)pyrazolidin-2-yl]heptanamide as in Example 1d.

e. Reduction of the ethanolic solution from Example 2d using NaBH$_4$ (0.7 g) and isolation of the product in a manner analogous to that used in Example 1d gave 3.0 g of 5. Purification by preparative HPLC (6% MeOH/EtOAc) gave 2.0 g of N(tert-amyl)7[3-oxo-1(3-hydroxy-n-octyl)pyrazolidin-2-yl]heptanamide (5) as an oil; HRMS analysis:

| measured | calcd. | assignment |
|---|---|---|
| 411.3451 | 411.3458 | C$_{23}$H$_{45}$N$_3$O$_3$ |
| 296.2328 | 296.2336 | M—C$_7$H$_{15}$O |

The pmr of this pure (by TLC) product was consistent with the assigned structure.

EXAMPLE 3

N(tert-Butyl)7[3-oxo-2-(3-hydroxy-n-octyl)pyrazolidin-1-yl]heptanamide (7), its hydrochloric acid salt (8) and its p-toluenesulfonic acid salt (9). (V=H$_2$, W=O, etc., as in Example 1)

a.

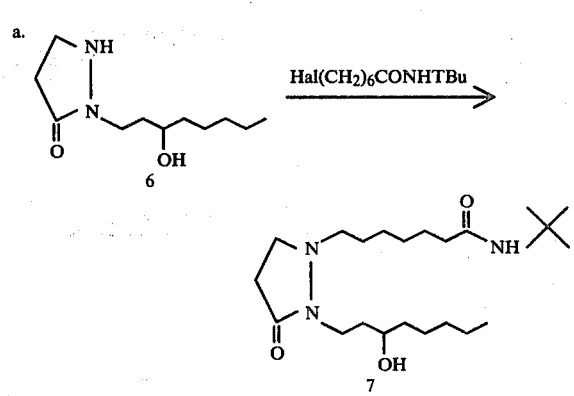

The 2(3-hydroxy-n-octyl)-3-pyrazolidinone (6) used in this and subsequent examples is prepared according to the General Synthetic Scheme (Ic) shown above and described in more detail in U.S. Pat. No. 3,873,566. A mixture of 3.85 g (18 mmoles) of pyrazolidinone alcohol 6 and 4.90 g (about 18 mmoles) of the N(tert-butyl)-7-bromo(chloro)heptanamide (Example 1a), 5.0g NaHCO$_3$, and 0.25 g NaI in 25 ml of tetramethylene sulfone was heated at 70° for about 56 hrs. The mixture was cooled, poured into 300 ml of H$_2$O and 5% NaOH was added to adjust the pH to 9. The mixture was extracted with ether twice. The combined ether extracts were washed with water and with saturated NaCl solution and dried over anhy. Na$_2$SO$_4$. The dry solution was filtered and treated with HCl gas until no more of the hydrochloride salt (8) separated (as a oil). The oil 8 was run into a separatory funnel, mixed with 50 ml of 5% Na$_2$CO$_3$ solution and extracted into ether. Evaporation of the ether after drying over Na$_2$SO$_4$ gave 3.01 g of N(tert-butyl)7[3-oxo-2(3-hydroxy-n-octyl)pyrazolidin-1-yl]heptanamide 7 which, according to TLC on silica gel (2:1 acetone-toluene; iodine; R$_f$0.37) was about 95% pure. The pmr spectrum (CDCl$_3$, TMS) agreed with the assigned structure (tert-butyl 1.33 ppm), as did the IR spectrum [$\lambda_{max}$ 3320, 3070 (weak, sharp), 1670-1650 (broad, strong) cm$^{-1}$]. A portion of this sample was further purified by preparative scale HPLC (6% MeOH/EtOAc) and analyzed by HRMS:

| measured | calcd. | assignment |
|---|---|---|
| 397.3341 | 397.3362 | $C_{22}H_{43}N_3O_3$ (M+) |
| 326.2440 | 326.2442 | M—$C_5H_{11}$ |
| 227.1735 | 227.1758 | M—$C_4H_9NHCO(CH_2)_5$ |

Another sample of N(tert-butyl)7[3-oxo-2-(3-hydroxy-n-octyl)pyrazolidin-1-yl]heptanamide (7) was prepared similarly by carrying out the reaction in tetramethylenesulfone for 47 hrs at 80°. The HPLC-purified sample (3.579 g, 7.00 mmoles) was dissolved in 2 ml of anhydrous acetonitrile and treated with 1.71 g (9.00 mmoles) of p-toluenesulfonic acid·H$_2$O in 3 ml of warm acetonitrile. Cooling at $-25°$ overnight and adding 5 ml of ether next morning gave 4.15 g (81%) of the p-toluenesulfonic acid salt (9) of 7 as a colorless solid, mp 121°–125°; $\lambda_{max}$ (Nujol) 3400, 3280, 2800-2000 (broad), 1742, 1645, 1561, 1162, 1033, 828, 691, 590 cm$^{-1}$; pmr (CDCl$_3$, TMS) at 60 MHz, 78 (tBu,i), 141 (pCH$_3$), 163 (CH$_2$CON, 3°) HZ etc.; Anal. Calcd. for $C_{29}H_{51}N_3O_6S$: C, 61.13; H, 9.02; N, 7.37; Found: C, 60.90; H, 8.95; N, 7.41.

EXAMPLE 4

N(2,2-Dimethylpropyl)7[3-oxo-2-(3-hydroxy-n-octyl)-pyrazolidin-1-yl]heptanamide (10) (V=H$_2$, W=0m=0n=5, Y=H, Z=CH$_2$(t)Bu, R$^1$=R$^2$=R$^3$=h, s=4, T=H)

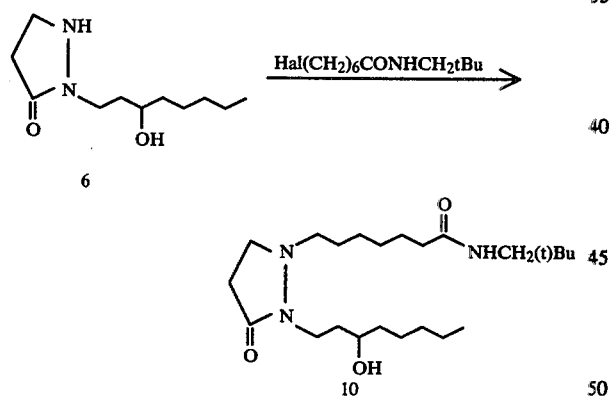

a. Neopentylamine (2equivalents) was added slowly to a solution of 7-bromo- and 7-chloroheptanoyl chloride in ether as described in the general procedure of Example 1a, giving the N(2,2-dimethylpropyl)7-haloheptanamide as an oil in about 75% yield; $\nu$ 3100, 3320, 1643, 1220 cm$^{-1}$; pmr (CDCl$_3$), δ 3.42 (tr, 2, J=7 Hz, HalCH$_2$), 3.05 (d, 2, J=7 Hz, CH$_2$NH), 2.17 (br, t, 2, J=7 Hz, CH$_2$CO), 0.88 ppm (s, 9, tert-Bu).

b. A mixture of 4.28 g (20 mmoles) of the pyrazolidinone 6, 5.56 g (20 mmoles) of N(2,2-dimethyl-propyl)7-haloheptanamide, 0.3 g of sodium iodide, and 2.55 g of sodium bicarbonate in 10 ml of DMF was heated at 100°±2° for 4.5 hrs with vigorous stirring. The mixture was cooled, poured into water and extracted with ether, which was washed successively with water and saturated NaCl solution, dried over anhyd. K$_2$CO$_3$, and evaporated, giving 7.1 g (86%) of crude amide 10. Purification by HPLC on silica gel (5% methanol/ethyl acetate) gave 5.57 g of pure amide 10 as a crystalline solid, mp 63°–65°; Anal. Calcd. for $C_{23}H_{45}N_3O_3$: C, 67.11; H, 11.02; N, 10.21; Found: C, 67.23; H, 10.96; N, 10.33.

EXAMPLE 5

N(1,1-Dimethylpropyl)7-[3-oxo-2(3-hydroxy-n-octyl)pyrazolidin-1-yl]heptanamide (11) and its p-toluenesulfonic acid salt (12). (V=H$_2$, W=O, etc. as in Ex. 4 except Z=C(CH$_3$)$_2$CH$_2$CH$_3$)

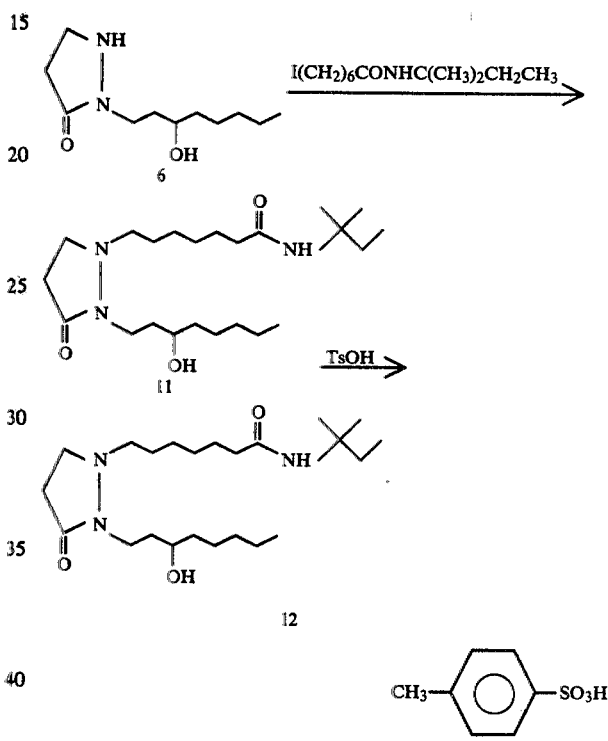

Pyrazolidinone 6 was treated with 1 equivalent of N(tert-amyl)7-iodoheptanamide (prepared as in Ex. 2a) and about 2 equivalents of NaHCO$_3$ in DMF at 110° for 2.5 hrs. Isolation of the pyrazolidinone carboxamide as described above, e.g. as Ex. 4, gave after purification by HPLC a 54% yield of 11 as a thick oil. Treatment of 11 with 1 equivalent of p-toluene-sulfonic in ether gave salt 12, which was recrystallized from acetonitrile; mp 102°–106°; Anal. Calcd. for $C_{30}H_{53}N_3O_6S$: C, 61.72; H, 9.15; N, 7.20; Found: C, 61.92; H, 9.02; N, 6.88.

EXAMPLE 6

N,N(Diisopropyl)7-[3-oxo-2(3-hydroxy-n-octyl)-pyrazolidin-1-yl]heptanamide (13). (V=H$_2$, W=O, etc. as in Ex. 4 except Y=Z=CH(CH$_3$)$_2$)

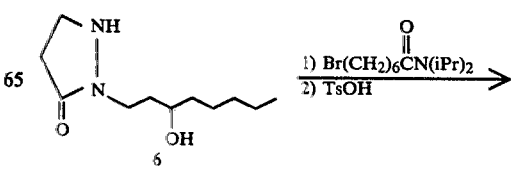

-continued

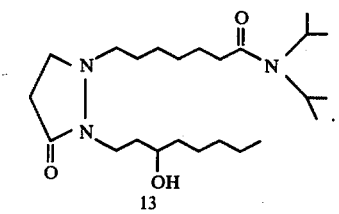
13

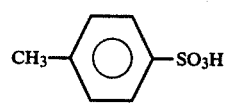

N,N-Diisopropylamine was converted to N,N-(diisopropyl)7-bromo(chloro)heptanamide in a manner analogous to the conversion of tert-butylamine to N(tert-butyl)7-bromo-(chloro)heptanamide, Example 1a.

A solution of 4.28 g (20 mmoles) of pyrazolidinone 6, 6.40 g (22 mmoles) of N,N(diisopropyl)7-bromo(-chloro)-heptanamide and 0.15 g of NaI in 20 ml of dry acetonitrile was heated at reflux for about 30 hrs. The mixture was cooled to room temp and a solution of 2.0 g (14.5 mmoles) of $K_2CO_3$ in 2.0 ml of water was added; after 0.5 hr of vigorous stirring an additional 2.0 g of anhydrous $K_2CO_3$ was added, the mixture was filtered, and the filtrate was evaporated. The remaining oil was partitioned between aqueous 5% $Na_2CO_3$ and ether. The ether layer was dried and evaporated, giving 7.05 g of crude product that was purified by HPLC using ethyl acetate as the eluent. The N,N-diisopropyl-7-[-3-oxo-2(3-hydroxy-n-octyl)pyrazolidin-1-yl]heptanamide was obtained as an oil (2.78 g), which showed the following m/e peaks in its high resolution mass spectrogram:

| measured | calcd. | assignment |
|---|---|---|
| 425.3621 | 425.3615 | $C_{24}H_{47}N_3O_3$ (M+) |
| 354.2766 | 354.2755 | M—$C_5H_{11}$ |
| 227.1755 | 227.1758 | M—[(CH$_2$)$_5$C(O)N(C$_3$H$_7$)] |

Reaction of this oil with 1 equivalent of p-toluene-sulfonic acid in ether gave the corresponding salt of (13), mp 69°–71°.

EXAMPLE 7

N(1,1,3,3,-Tetramethyl-n-butyl)7[3-oxo-2(3-hydroxy-n-octyl)pyrazolidin-1-yl]heptanamide (14) (V=H$_2$, W=O, m=O, n=5; Y=H, Z=C(CH$_3$)$_2$CH$_2$C(CH$_3$)$_3$, R$^1$=H, R$^2$=H, R$^3$=H, s=4, T=H)

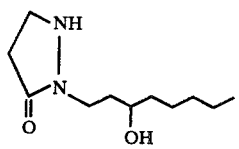
14

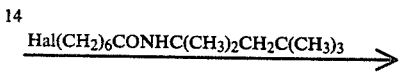

-continued

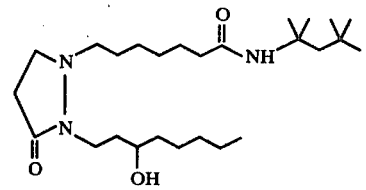
14 tert-Octylamine was converted to N,N(1,1,3,3-dimethyl)7-bromo(chloro)heptanamide by a procedure analogous to that described in Example 1a for the preparation of N(tert-butyl)7-bromo(chloro) heptanamide. The amide was allowed to react with pyrazolidinone 6 and the resulting product 14 was purified in a manner analogous to the synthesis of 10, Example 4b. Pure N(1,1,3,3-tetramethyl-n-butyl)7[3-oxo-2(3-hydroxy-n-octyl)-pyrazolidin-1-yl]heptanamide (14) was obtained as an oil; HRMS m/e measured 453.3902; calculated for $C_{26}H_{51}O_3N_3$ 453.3927. The sample showed a single spot (R$_f$ ea. 0.4) on silica gel TLC (5% methanol/CH$_2$Cl$_2$).

EXAMPLE 8

N(iso-Propyl)7[3-oxo-2(3-hydroxy-n-octyl)pyrazolidin-1-yl]heptanamide (15) and its p-toluenesulfonate salt (16)

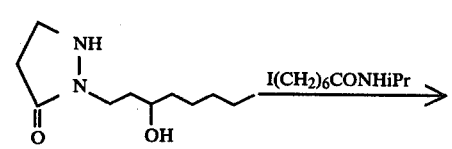

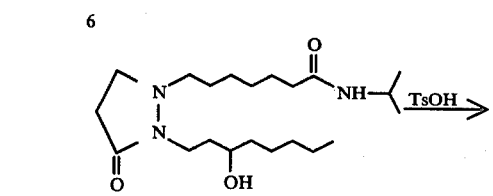
15

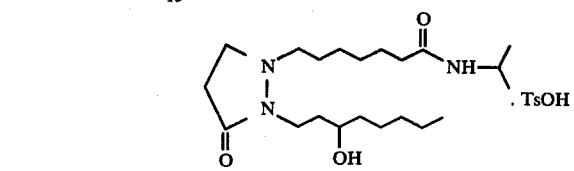
16

Two and two tenths molar equivalents of isopropylamine was allowed to react with one molar equivalent of a mixture of 7-bromo- and 7-chloroheptanamide according to the procedure of Example 1a, giving the N-isopropyl-7-haloheptanamide as a viscous oil. A solution of this amide and NaI in methyl ethyl ketone was heated at reflux temperature for 22 hrs, giving N-isopropyl 7-iodoheptanamide, isolated as a solid, mp 46°–51°; pmr (CDCl$_3$) δ 3.22 (t, CH$_2$I), 1.13 ppm [d, CH(CH$_3$)$_2$].

This iodamide was treated with pyrazolidinone 6 by a procedure analogous to that used for the synthesis of 10, Example 4b. The crude product 15, was obtained as an oil in 94% yield. A solution of 6.84 g of 15 in 3 ml of dry acetonitrile was added to a solution of 3.39 g of p-toluenesulfonic acid in 26 ml of dry acetonitrile, giving 5.12 g (66%) of salt 16, mp 123°–126°. Recrystallization from acetonitrile gave analytically pure salt 16, mp 129°–130.5°; Anal. calcd. for $C_{28}H_{49}N_3SO_6$: C, 60.51; H, 8.89; N, 7.56; found C, 60.50; H, 8.75; N, 7.89. The pka of this salt, measured in 1:1 ethanol/water, was found to be 3.25.

EXAMPLE 9

N-methyl-7[3-oxo-2(hydroxy-n-octyl)pyrazolidin-1-yl]heptanamide (17)

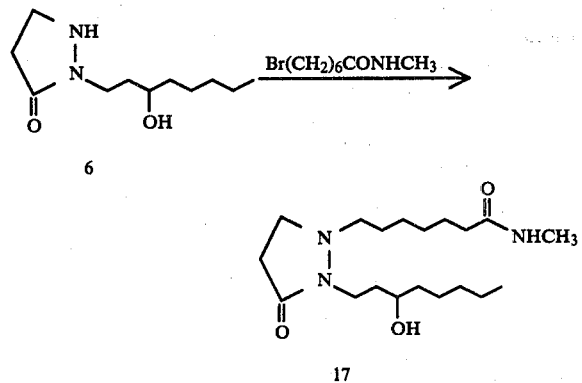

A solution of 1.92 g (61.8 mmoles) of anhydrous methylamine in 50 ml ether was added dropwise to a solution of 30 mmoles of 7-bromo(chloro)heptanoylchloride in ether at 0°. The product of the reaction, N-methyl-7-bromo(chloro)heptanamide, isolated in a manner analogous to the procedure described in Example 1 a, was a white solid, mp 48°–9°.

N-methyl-7-bromo(chloro)heptanamide (15 mmoles), pyrazolidinone 6 (3.21 g, 15 mmoles), magnesium oxide (1.2 g), and NaI (0.15 g) in 25 ml of dimethylsulfoxide were stirred at room temperature for 7 days and then the mixture was heated at 100° for 18 hrs. The mixture was cooled, poured into 150 ml of water, and extracted with ether. The ether was washed with water, dried, and evaporated, giving 3.8 g of an amber oil that was purified by high pressure liquid chromatography on silica gel using 5% methanol/ethyl acetate gave 2.3 g of N-methyl 7[3-oxo-(3-hydroxy-n-octyl) pyrazolidin-1-yl] heptanamide (17) as an oil; HRMS m/e measured 355.2863, calcd. for $C_{19}H_{37}N_3O_3$ 355.2894 (M+); TLC (2:1 acetone/toluene) $R_f$=ca. 0.07; pmr (CDCL$_3$) was in agreement ($\delta$ 2.75 ppm, d, for NHCH$_3$).

The $\omega$-halo carboxylic acids of Column A can be converted to the corresponding acid chlorides by means of the action of SOCl$_2$ according to the general methods described in Example 1a. These acid chlorides on treatment with the corresponding amines of Column B give the corresponding $\omega$-halo amides of Column C. (For example, the $\omega$-halo acid (a) of Col. A, and amine (a) of Col. B, give halo amine (a) of Col. C; $\omega$-halo acid (b) and amine (b) give halo amide (b), etc.) It is to be understood that although the halo amides of Col. C are the major products obtained, in each case a smaller amount of the corresponding chloro amide is obtained as in Example 1a, and that mixture of these chloro and bromo amides can be converted to a single iodo compound as described in Example 1a. Whether a given amide is $\omega$-substituted with bromo, chloro, or iodo makes little difference as far as its use in preparing the compounds of Cols. D, L, or M.

3-Pyrazolidinone Carboxamides where V=O and W=H$_2$

The preparation of 1-benzyloxycarbony-3-pyrazolidinone (I) from 3-pyrazolidinone.HCl and benzyloxycarbonyl chloride is described in U.S. Pat. No. 3,873,566. Reaction of I with halo amides (a), (c), (e), (g), (i), (k), or (m) of Col. C according to the procedure of Example 1b affords the corresponding pyrazolidinyl amides of Col. D. Hydrogenolysis of the carbobenzoxy protecting groups of the compounds of Col. D according to the procedures analogous to those described in Example 1c affords the corresponding pyrazolidinyl amides of Col. E. The compounds of Col. E are allowed to react with the vinyl ketones of Col. F to afford Michael adducts which on reaction with methylmagnesium halide, or methyllithium at about $-60°$, afford the corresponding tertiary alcohols. In the case of the Michael adducts derived from the vinyl ketones of Col. F, (a), (g), and (k), the tertiary alcohols obtained from those of Col. G. Or, the Michael adducts derived from vinyl ketones of Col. F, (c), (e), (i) and (m) can be reduced with NaBH$_4$ in ethanol as described in Example 1e, to afford the corresponding secondary alcohols of Col. H.

3-Pyrazolidinones where V=H$_2$ and W—O

Reactions of I with the vinyl ketones in the presence of a basic catalyst (e.g. Triton® B) is described in U.S. Pat. No. 3,873,566. The Michael adducts obtained in this manner, e.g. by reaction of the vinyl ketones of Col. I, can be reduced with NaBH$_4$ and then subjected to catalytic hydrogenolysis, to obtain the corresponding pyrazolidinyl alcohols of Col. J, or the adducts can be treated with methylmagnesium halide or with methyllithium to obtain, after catalytic hydrolysis, the pyrazolidinyl alcohols of Col. K.

By procedures analogous to that used in Example 3, the pyrazolidinyl alcohols of Col. K are treated with the corresponding halo amide (j) and (n) of Col. C affording the products of Col. M. Or, the pyrazolidinyl alcohols of Col. J are similarly treated with the corresponding halo amides of Col. C to afford the corresponding pyrazolidinone amides of Col. L.

| Col. A ($\omega$-Halo Acids) | Col. B (Amine) |
|---|---|
| (a) BrCH$_2$C≡C(CH$_2$)$_3$CO$_2$H | (a) (CH$_3$)$_3$CCH$_2$NH$_2$ |
| (b) BrCH$_2$C≡C(CH$_2$)$_3$CO$_2$H | (b) (iC$_3$H$_7$)$_2$NH |
| (c) ICH$_2$C≡C(CH$_2$)$_3$CO$_2$H | (c) C$_2$H$_5$C(CH$_3$)$_2$NH$_2$ |
| (d) BrCH$_2$CH=CH(CH$_2$)$_3$CO$_2$H | (d) tert C$_4$H$_9$NH$_2$ |
| (e) BrCH$_2$CH=CH(CH$_2$)$_3$CO$_2$H | (e) (C$_2$H$_5$)$_2$NH |
| (f) BrCH$_2$CH=CH(CH$_2$)$_3$CO$_2$H | (f) iC$_3$H$_7$NHCH$_3$ |
|  | (g) iC$_3$H$_7$NH$_2$ |
| (g) BrCH$_2$—⟨O⟩—CH$_2$CO$_2$H |  |
|  | (h) CH$_3$NH$_2$ |
| (h) BrCH$_2$—⟨O⟩—CH$_2$CH$_2$CO$_2$H |  |
|  | (i) nC$_5$H$_{11}$NH$_2$ |
| (i) ClCH$_2$—⟨O⟩—(CH$_2$)$_3$CO$_2$H |  |
| (j) Br(CH$_2$)$_6$CO$_2$H | (j) nC$_{12}$H$_{25}$NH$_2$ |
| (k) Br(CH$_2$)$_6$CO$_2$H | (k) tert C$_4$H$_9$NH$_2$ |
| (l) Br(CH$_2$)$_6$CO$_2$H | (l) (CH$_3$)$_3$CCH$_2$C(CH$_3$)$_2$NH$_2$ |
| (m) Hal(CH$_2$)$_6$CO$_2$H | (m) NH$_3$ |

-continued

| Col. A (ω-Halo Acids) | Col. B (Amine) |
|---|---|
| (n) I(CH$_2$)$_6$CO$_2$H | (n) nC$_6$H$_{13}$NH$_2$ |

Col. C (Halo Amide)
(ex. Cols. A + B)
(a) BrCH$_2$C≡C(CH$_2$)$_3$CONHCH$_2$C(CH$_3$)$_3$
(b) BrCH$_2$C≡C(CH$_2$)$_3$CON(C$_3$H$_7$i)$_2$
(c) ICH$_2$C≡C(CH$_2$)$_3$CONHC(CH$_3$)$_2$C$_2$H$_5$
(d) BrCH$_2$CH=CH(CH$_2$)$_3$CONHC$_4$H$_9$(tert)
(e) BrCH$_2$CH=CH(CH$_2$)$_3$CON(C$_2$H$_5$)$_2$
(f) BrCH$_2$CH=CH(CH$_2$)$_3$CON(CH$_3$)C$_3$H$_7$(i)

(g) 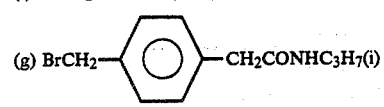

(h) 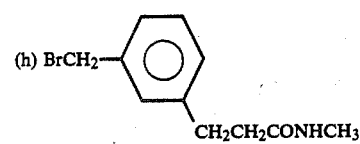

(i) 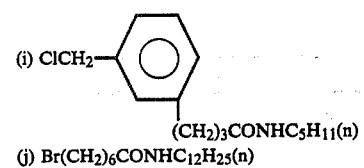

(j) Br(CH$_2$)$_6$CONHC$_{12}$H$_{25}$(n)
(k) Br(CH$_2$)$_6$CONHC$_4$H$_9$(tert)
(l) Br(CH$_2$)$_6$CONHC(CH$_3$)$_2$CH$_2$C(CH$_3$)$_3$
(m) Hal(CH$_2$)$_6$CONH$_2$
(n) I(CH$_2$)$_6$CONHC$_6$H$_{13}$(n)

Col. D
(ex. Col. C)

(a) 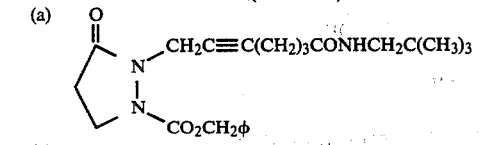

(b) —
(c) 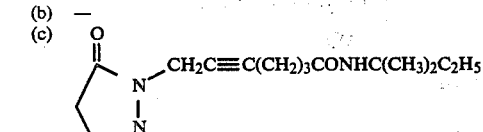

(d) —
(e) 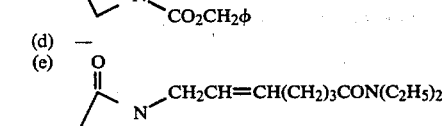

(f) —
(g) 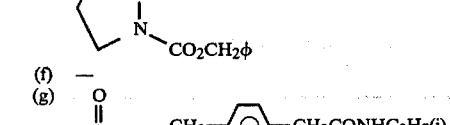

(h) —
(i) 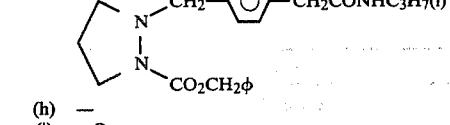

Col. D (j) —
(k) 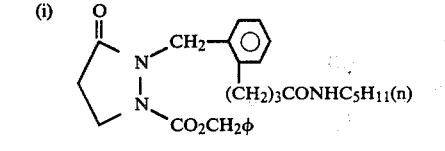

(l) —
(m) 

(n) —

Col. E
(ex. Col. D)

(a) 

(b) —
(c) 

(d) —
(e) CH$_2$CH=CH(CH$_2$)$_3$CON(C$_2$H$_5$)$_2$ attached to pyrazolidinone (f) —
(g) CH$_2$–phenyl–CH$_2$CONHC$_3$H$_7$(i) attached to pyrazolidinone (h) —
(i) CH$_2$–phenyl–(CH$_2$)$_3$CONHC$_5$H$_{11}$(n) attached to pyrazolidinone (j) —
(k) (CH$_2$)$_6$CONHC$_4$H$_9$(tert) attached to pyrazolidinone (l) —
(m) (CH$_2$)$_6$CONH$_2$ attached to pyrazolidinone (n) —

Col. F
(Vinyl Ketones)

(a)  CH$_2$=CHCOC$_5$H$_{11}$(n)

Col. F
(Vinyl Ketones)

- (b) —
- (c) $CH_2=CHCOCF_2(CH_2)_4CH_3$
- (d) —
- (e) $CH_2=CHCOC(CH_3)_2(CH_2)_4H$
- (f) —
- (g) $CH_2=CHCOC_5H_{11}(n)$
- (h) —
- (i) $CH_2=CHCOCH(CH_3)(CH_2)_4H$
- (j) —
- (k) $CH_2=CHCO(CH_2)_4CF_3$
- (l) —
- (m) $CH_2=CHCOC_6H_{13}(n)$

Col. G
(ex. Cols. E + F)

(a) 
<chemical structure: pyrazolidinone with N—CH₂C≡C(CH₂)₃CONHCH₂C(CH₃)₃ and N—CH₂CH₂C(CH₃)(OH)—C₅H₁₁(n)>

(g)
<chemical structure: pyrazolidinone with N—CH₂—C₆H₄—CH₂CONHC₃H₇(i) and N—CH₂CH₂C(CH₃)(OH)—C₅H₁₁(n)>

(k)
<chemical structure: pyrazolidinone with N—(CH₂)₆CONHC₄H₉(tert) and N—CH₂CH₂C(CH₃)(OH)(CH₂)₄CF₃>

Col. H
(ex. Cols. E + F)

(c)
<chemical structure: pyrazolidinone with N—CH₂C≡C(CH₂)₃NHC(CH₃)₂C₂H₅ and N—CH₂CH₂CHCF₂(CH₂)₄CH₃ with OH>

(e)
<chemical structure: pyrazolidinone with N—CH₂CH=CH(CH₂)₃CON(C₂H₅)₂ and N—CH₂CH₂CHC(CH₃)₂(CH₂)₄H with OH>

(i)
<chemical structure: pyrazolidinone with N—CH₂—C₆H₄—(CH₂)₃CONH(5H₁₁)(n) and N—CH₂CH₂CHCH(CH₃)(CH₂)₄H with OH>

Col. H
(m)
<chemical structure: pyrazolidinone with N—(CH₂)₆CONH₂ and N—CH₂CH₂CHC₆H₁₃(n) with OH>

Col. I
(vinyl ketones)

- (b) $CH_2=CHCOC_7H_5(n)$
- (d) $CH_2=CHCOCHF(CH_2)_3CF_3$
- (f) $CH_2=CHCOCH(CH_3)(CH_2)_6H$
- (h) $CH_2=CHCO(CH_3)_2(CH_2)_4CF_2CH_3$
- (j) $CH_2=CHCOC_5H_{11}(n)$
- (l) $CH_2=CHCOCHFCH_2CF_2CH_3$
- (n) $CH_2=CHCOC_6H_{13}(n)$

Col. J
(ex. Col. I)

(b)
<hydrazide structure: O=C—NH—N—CH₂CH₂CHC₇H₁₅(n) with OH>

(d)
<hydrazide structure: O=C—NH—N—CH₂CH₂CHCHF(CH₂)₃CF₃ with OH>

(f)
<hydrazide structure: O=C—NH—N—CH₂CH₂CHCH(CH₃)(CH₂)₆H with OH>

(h)
<hydrazide structure: O=C—NH—N—CH₂CH₂CHC(CH₃)₂(CH₂)₄CF₂CH₃ with OH>

(l)
<hydrazide structure: O=C—NH—N—CH₂CH₂CHCHFCH₃CF₂CH₃ with OH>

Col. K
(ex. Col. I)

(j)
<hydrazide structure: O=C—NH—N—CH₂CH₂C(CH₃)(OH)—C₅H₁₁(n)>

-continued

Col. K (n) 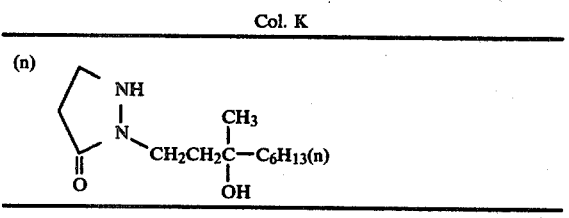

Col. L (ex. Cols. C + J)

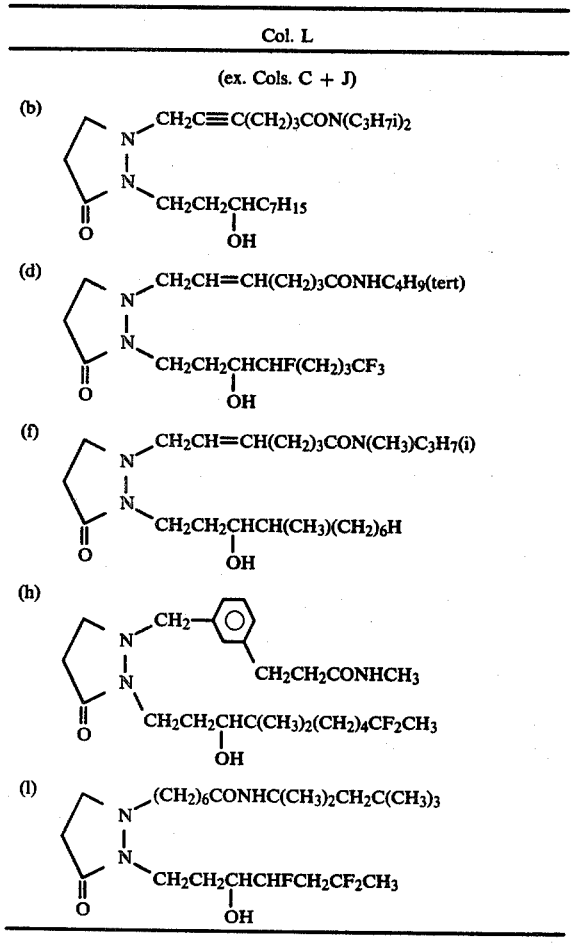

Col. M (ex. Cols. G + K)

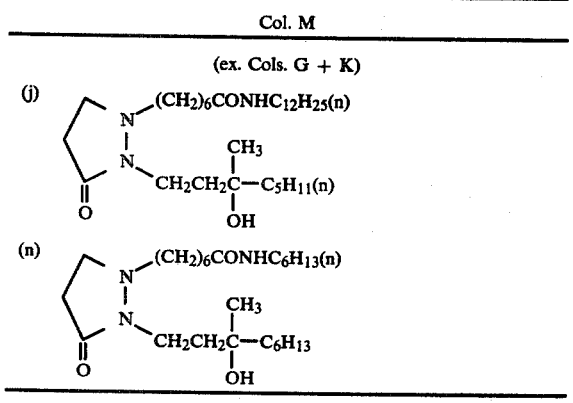

EXAMPLE 10

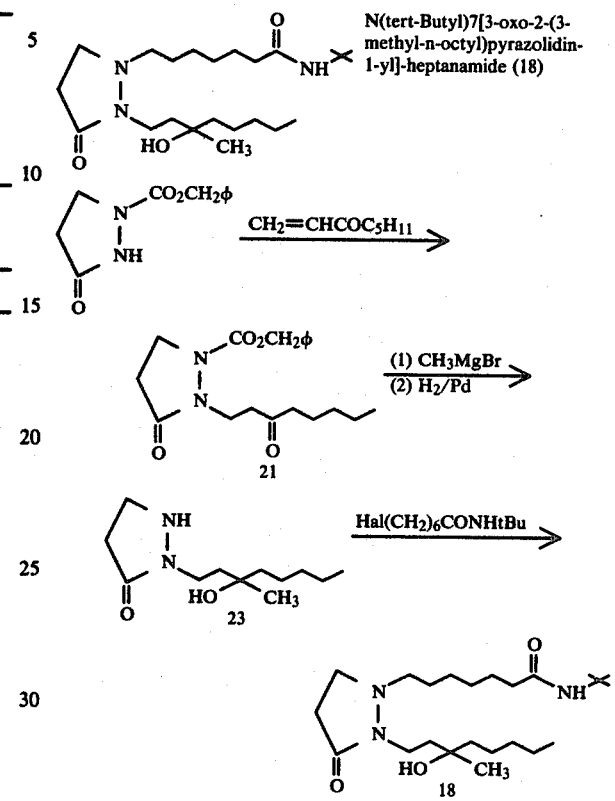

N(tert-Butyl)7[3-oxo-2-(3-methyl-n-octyl)pyrazolidin-1-yl]-heptanamide (18)

1-Benzyloxycarbonyl-3-pyrozolidianone is treated with amyl vinyl ketone in ethanol as described in U.S. Pat. No. 3,873,566. The ethanolic solution of the Michael adduct is acidified with a little acetic acid, evaporated, and taken up in ether. Washing the ether solution with 5% NaHCO$_3$, drying, and evaporation gives pure 1-benzoyloxycarbonyl-2(3-oxo-n-octyl)-3-pyrazolidinone (22) ($\gamma$max 1720, 1500 cm$^{-1}$). This oil is dissolved in tetrahydrofuran and the solution evaporated to remove traces of ethanol. A solution of the oil in fresh tetrahydrofuran is then cooled to $-78°$ and treated by the addition of 1 mole equivalent of methylmagnesium bromide. The solution is allowed to gradually warm to room temperature and the crude produced is purified by chromatography on silica gel, affording 1-benzoyloxycarbonly-2(3-hydroxy-3-methy-n-octyl)3-pyrazolidinone (23).

In a manner analogous to the preparation of Compound 7, Example 3, the pyrazolidinone 23 is treated with N-(tert-butyl)7-bromo(chloro) heptanamide to give, after purification of the product by chromatography, compound 18.

EXAMPLE 11

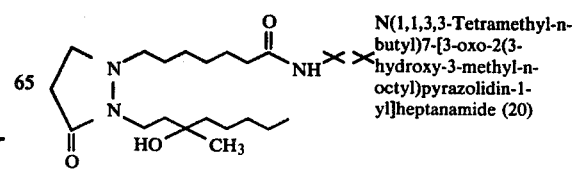

N(1,1,3,3-Tetramethyl-n-butyl)7-[3-oxo-2(3-hydroxy-3-methyl-n-octyl)pyrazolidin-1-yl]heptanamide (20)

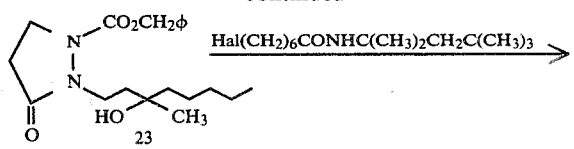

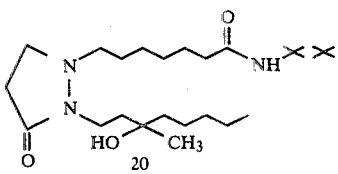

In a manner analogous to the preparation of compound 14, Example 7, the pyrazolidinone 23 is converted by action of N(1,1,3,3-tetramethyl)7-bromo(chloro) heptanamide to 20.

EXAMPLE 12

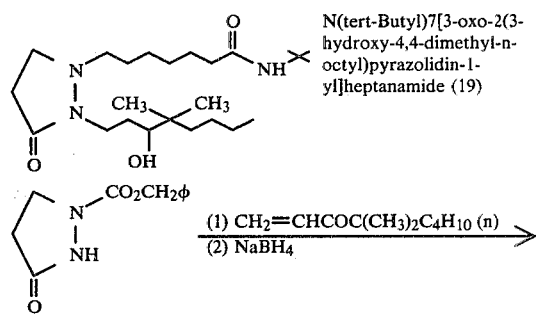

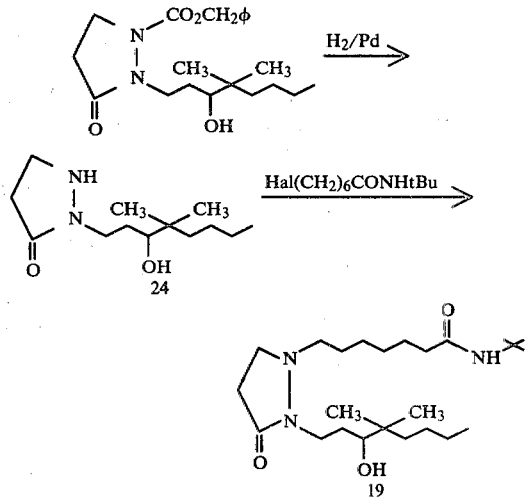

The preparation of 4,4-dimethyl-1-octene-3-one is outlined in U.S. Pat. No. 3,873,566. This vinyl ketone is allowed to react with 1-benzyloxycarbonyl -3-pyrazolidinone in a manner analogous to the reaction of the vinyl ketone of Example 10. The ethanolic solution of the Michael adduct is treated with sodium borohydride in a manner analogous to the preparation of the previously described 2(3-hydroxy-n-octyl)-3-pyrozolidinone 6 (Example 3), giving, after after isolation by chromatography or silica gel, 2(3-hydroxy-4-dimethyl-n-octyl)3-pyrazolidinone (24).

In a manner analogous to the preparation of compound 7, Example 3, the pyrazolidinone 24 is treated with N(tert-butyl)7-bromo (chloro) heptanamide to give after purification of the product by chromatography compound 19.

EXAMPLE 13

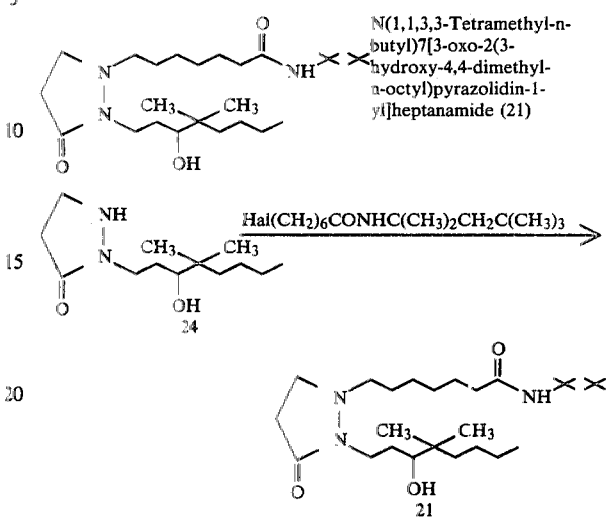

In a manner analogous to the preparation of Compound 14, Example 7, the pyrazolidinone 2 is treated with N (1,1,3,3-tetramethyl)7-bromo(chloro) heptanamide to give, after purification by chromatography on silica gel the carboxamide 21.

The pyrazolidinone amides of this invention are prostaglandin antagonists, i.e., they inhibit the effects of natural prostaglandins such as $PGE_1$. Prostaglandin antagonists are widely recognized as being of potential use for the control of diarrhea and of possible use as anti-inflammatory agents. They are also recognized as being of potential use for the clinical study of disorders that might involve excessive levels of endogenous prostaglandins in humans or animals. Finally, there is a recognized need for prostaglandin antagonists to facilitate the scientific investigation of the roles of natural prostaglandins in biological systems.

U.S. Pat. No. 3,873,566 described diazaprostaglandin analog esters, many of which were prostaglandin antagonists. The corresponding diazaprostaglandin analog carboxylic acids were generally prostaglandin mimics. It is well known that many long chain fatty acid esters ordinarily undergo hydrolysis in vivo by processes involving general esterase enzymes. Also some esters, particularly tert-butyl esters, can be hydrolyzed slowly by stomach acid. Thus when the diazaprostanoid esters are administered to test animals they show some of the side effects typical of prostaglandins, e.g., diarrhea; these side effects presumably are due, at least in part, to hydrolysis in vivo to the diazaprostaglandin carboxylic acids.

It is well known that carboxamides are more resistant toward hydrolysis than carboxylic acid esters. Surprisingly, the amides of this invention exhibit prostaglandin antagonist acitivity. In addition to be more stable than the corresponding esters, the amides of this invention are higher melting and hence easier to isolate and purify either as crystalline solids themselves or as crystalline salts, e.g., as p-toluenesulfonic acid salts.

Test results which indicate the prostaglandin antagonist activity for the compounds of this invention are listed below in Table 1.

TABLE 1

| Example No. | Compound No. | PGE$_1$ Antagonist IC$_{50}$, μg/ml |
| --- | --- | --- |
| 1 | 1 | 60 |
| 2 | 5 | 25 |
| 3 | 7 | 33 |
| 3 | 9 | 60 |
| 4 | 10 | 3-5 |
| 5 | 12 | 5 |
| 6 | 13 | 20 |
| 7 | 14 | 2 |
| 8 | 16 | 75 |
| 9 | 17 | 175 |

The rat stomach assay from which these data are derived is based on the method of J. R. Vane [Brit. J. Pharmacol. 12, 344 (1957)]. Male rats are decapitated and a strip is cut from the fundus of the stomach along the greater curvature. The strip (3 to 5 mm wide and 3 to 4 cm long) is suspended in Tyrode solution at pH 7.1 and 37° and gassed continuously with oxygen. Responses of the muscle are monitored isometrically by means of a strain gauge transducer. The above table lists for several compounds of this invention the concentration in μg/ml required to inhibit by 50% the contraction of muscle strips caused by a concentration of PG$_1$ that normally causes about 25% of maximum responses (about μg/ml). Some of the carboxamides were also run against higher concentration of PGE$_1$ and gave greater IC$_{50}$ values. This suggests that the autogonism is at least partially competitive.

Surprisingly, some of these compounds also inhibit the formation of experimentally-induced gastric ulcers in rats—even though such inhibition is usually associated with prostaglandin mimics, i.e., smooth muscle agonists instead of antagonists. One of these compounds is the tert-butylcarboxamide 7 of Example 3. In a test designed to detect gastric cytoprotectin [Robert, U.S. Pat. No. 4,097,603], compound 7 inhibited ethanol-induced gastric ulcer to the extent of about 50 % when administered orally to rats at 2 mg/kg. Under similar conditions 0.5 mg/kg of PGE$_1$ inhibited ulcer formation to the extent of 80%. Unlike PGE$_1$, however, carboxamide 7 and its salts of physiologically acceptable acids, has no overt prostaglandin-like side effects when administered orally to rats. For example, at doses as high as 300 mg/kg it causes no mortality or diarrhea. At 2.0 mg/kg compound 14 of Example 7 gave about 18% protection and compound 16 of Example 8 gave about 27% protection against ulcers.

What is claimed is:

1. A compound of the formula

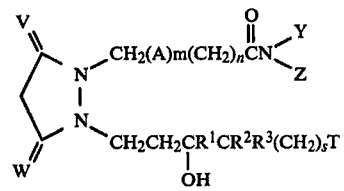

and salts with pharmaceutically acceptable acids where V or W is O and the other is H$_2$;

A is CH=CH, C≡C or phenylene;

m is 0-1;

n is 1-5, with the proviso that when m=0,
n is 5 and when m is 1 and A is CH=CH or C≡C,
n is 1, 2 or 3;

Y and Z are either the same or different and are selected from the group consisting of H, and C$_1$-C$_{12}$ straight-chain or branched-chain alkyl;

R$^1$ is H, CH$_3$, C$_2$H$_5$, CH=CH$_2$ or C≡CH;

R$^2$ is H, F, Or CH$_3$;

R$^3$ is H, F, or CH$_3$, with the proviso that when R$^1$≠H, R$^2$ and R$^3$ are H;

S is 3-6; and

T is H, CF$_2$CH$_3$ or CF$_3$.

2. A compound of claim 1 which is N(tert-amyl)7 [3-oxo-1(3-hydroxy-n-octyl)pyrazolidin-2-yl]heptanamide.

3. A compound of claim 1 which is N(tert-butyl)7-[3-oxo-2-(3-hydroxy-n-octyl)pyrazolidin-1-yl]-heptanamide.

4. A compound of claim 1 which is N(2,2-dimethylpropyl)-7-[3-oxo-2-(3-hydroxy-n-octyl)pyrazolidin-1-yl]-heptanamide.

5. A compound of claim 1 which is N,N(diisopropyl)7-[3-oxo-2-(3-hydroxy-n-octyl)pyrazolidin-1-yl]heptanamide.

6. A compound of claim 1 which is N(1,1,3,3-tetramethyl-n-butyl)7 [3-oxo-2-(3-hydroxy-n-octyl)-pyrazolidin-1-yl]-heptanamide.

7. A compound of claim 1 which is N(tert-butyl)7[3-oxo-2-(3-methyl-n-octyl)pyrazolidin-1-yl]-heptanamide.

8. A compound of claim 1 which is N(1,1,3,3-tetramethyl-n-butyl)7-[3-oxo-2(3-hydroxy-3-methyl-n-octyl)-pyrazolidin-1-yl]heptanamide.

9. A compound of claim 1 which is N(tert-butyl)7 [3-oxo-2(3-hydroxy-4,4-dimethyl-n-octyl)-pyrazolidin-1-yl]-heptanamide.

10. A compound of claim 1 which is N(1,1,3,3-tetramethyl-n-butyl)7[3-oxo-2(3- hydroxy-4,4-dimethyl-n-octyl) pyrazolidin-1-yl]heptanamide.

* * * * *